(12) United States Patent
Zeligs (10) Patent No.: US 6,534,085 B1
(45) Date of Patent: Mar. 18, 2003

(54) PHYTOCHEMICALS FOR PROMOTING WEIGHT LOSS

(75) Inventor: Michael A. Zeligs, Boulder, CO (US)

(73) Assignee: BioResponse L.L.C., Boulder, CO (US)

( * ) Notice: Subject to any disclaimer, the term of this patent is extended or adjusted under 35 U.S.C. 154(b) by 0 days.

(21) Appl. No.: 09/404,112

(22) Filed: Sep. 23, 1999

(51) Int. Cl.⁷ ................................................ A61K 9/48
(52) U.S. Cl. .................. 424/451; 424/464; 424/450; 424/458; 424/488; 424/489; 424/486; 424/401; 424/439; 424/45; 424/725; 424/736; 514/323
(58) Field of Search .................. 514/323, 899; 424/450, 451, 458, 501, 488, 489, 486, 464, 401, 439, 45

(56) References Cited

U.S. PATENT DOCUMENTS 4,617,298 A * 10/1986 Bodor et al. ................ 514/176
5,830,887 A * 11/1998 Kelly ........................... 514/182
6,086,915 A * 7/2000 Zeligs et al. ................. 424/455

* cited by examiner

Primary Examiner—Thurman K. Page
Assistant Examiner—Liliana DiNola-Baron
(74) Attorney, Agent, or Firm—Pennie & Edmonds LLP (57) ABSTRACT

New dietary supplement compositions are disclosed that comprise the phytochemical Diindolylmethane (DIM), as well as its precursor, Indole-3-carbinol (I3C), and cogener, 2-(Indol-3-ylmethyl)-3,3' diindolylmethane (LTR-1), dietary supplement acceptable carriers and/or excipients. The use of these dietary supplement compositions facilitate weight loss as part of a nutritional system targeting release and metabolism of stored fat.

34 Claims, 4 Drawing Sheets

PHYTOCHEMICALS FOR PROMOTING WEIGHT LOSS

1. INTRODUCTION

The present invention relates to compositions and methods for promoting weight loss and/or preventing weight gain in mammals by administering phytochemicals. Among the phytochemicals useful in the compositions and methods of the invention are dietary indole, Diindolylmethane (DIM), as well as its precursor, Indole-3-carbinol (I3C), and cogener, 2-(Indol-3-ylmethyl)-3,3'-diindolylmethane (LTR-1). When used as described, these natural substances, alone and in combination with other substances, facilitate weight loss as part of a nutritional system targeting release and metabolism of stored fat.

2. BACKGROUND OF THE INVENTION

The term "overweight" describes an excessive accumulation of body fat or "adiposity". "Overweight" is defined as an elevation in the Body Mass Index (BMI) beyond desirable standards due to increased body fat. The BMI expresses an individual's degree of overweight independent of height by dividing weight in kilograms (Kg) by height squared ($m^2$). In overweight men a BMI above 25 $Kg/m^2$ and in overweight women a BMI above 26 $Kg/m^2$ defines a level of adiposity which negatively impacts health (Simopoulos, A.P., Body Weight Reference Standards, In Van Itallie, T.B. and Simopoulos, A.P. (Eds), Obesity: New Directions in Assessment and Management, The Charles Press, Inc., Philadelphia, Pa., 1995). The increasing prevalence of overweight is one of the major health problems of industrialized countries. Overweight occurs as a result of an imbalance between energy intake as food and energy expenditure through physical activity. Most importantly, the trend to increased consumption of sugar and refined carbohydrate in excess of energy needs results in a metabolic and hormonal status favoring the formation and storage of fat. Weight loss depends on mobilization and metabolism of fat at the cellular level. This requires the metabolic process of lipolysis and encompasses the release of stored fat from fat cells. In all mammals the process and rate of lipolysis are highly regulated by the system of catecholamine hormones.

Increased carbohydrate consumption in modern society is the result of the introduction of refined sugar and processed carbohydrate in various forms. The addition of high fructose corn syrup in 1967 is a prime example of this shift in dietary composition which has contributed to the further increase of the sugar component of the average diet to about 8% of total calories (Raper, N., and Marston, R., "Content of the U.S. food supply (tables of nutrients and foods)", Human Nutrition Information Service: Washington, D.C., U.S. Department of Agriculture, 1988). The presence of sugar and other "high glycemic" processed carbohydrates found in bread and pasta, increases blood insulin levels, inhibits lipolysis, and promotes new fat synthesis. This raises serum triglycerides, serum cholesterol, and increases the risk of atherosclerosis and coronary heart disease. Strategies to decrease our daily intake of processed carbohydrate and increase the release and metabolism of stored fat are clearly needed.

Interventions to decrease appetite have focused on supporting brain levels of the neurotransmitter serotonin which is derived from the amino acid tryptophan. However, simply providing increased dietary sources of tryptophan have in themselves not proven successful at reducing appetite. Use of drugs such as fluoxetine and fenfluramine, which raise brain serotonin levels, have proven effective in promoting weight loss. Unfortunately, this pharmacologic approach has been recently associated with serious cardiovascular side effects (Kolanowski, J., "A risk-benefit assessment of anti-obeisity drugs", Drug Safety 20(2):119–131, 1999). Use of the serotonin precursor, L-5-hydroxy-tryptophan (5HTP) may represent a safer approach to reducing appetite for carbohydrates. Other safe and effective means to promote weight loss are clearly needed.

With regard to increasing fat metabolism, both caloric restricted dieting and increased exercise promote a more active catecholamine system which favors active lipolysis. Increasing the efficiency of this process has been the object of much of the pharmacotherapy of obesity.

The process of lipolysis is regulated primarily by the system of catecholamine hormone receptors present on the surface of fat cells. These catecholamine receptors consist of a family of membrane bound proteins with differerent structure and activity known as the $\alpha$ and $\beta$ receptors. The $\alpha$ and $\beta$ receptors have opposing action on the rate of lipolysis. Predominance of activity from the $\beta$ receptors favors active lipolysis and translates into weight loss. Predominance of $\alpha$ receptor activity inhibits lipolysis and favors continued fat storage. Nature has provided for an adaptive mechanism by which activity and number of the a receptors increase with caloric restriction. This slows continued lipolysis during periods of fasting and results in the increased loss of muscle tissue in addition to fat during dieting. The increased presence and activity of $\alpha$ receptors and decreased overall metabolic rate which occur during fasting has been call the "starvation response". The starvation response reduces the efficiency of lipolysis during weight loss.

Much of modern obesity research has concerned methods for maintaining a hormonal balance which favors $\beta$ over $\alpha$ receptor activity to promote more efficient and active lipolysis. The objective is to facilitate continued lipolysis or fat loss while preserving muscle or "lean body mass". This is achieved with exercise, a restricted calorie but protein supplemented diet, and with the administration of substances which mimic the $\beta$ receptor activity of the catecholamine hormones. The most popular $\beta$ stimulating substance in use since antiquity is ephedrine, originally discovered in the Chinese herb "Ma Huong". Ephedrine resembles the catecholamine hormone, epinephrine, and effectively increases the rate of lipolysis. However, like epinephrine, ephedrine produces serious side effects related to overstimulation of the sympathetic nervous system, including tachycardia, hypertension, nervousness, tremor and insomnia (Cupp, M. J., "Herbal remedies: adverse effects and drug interactions", American Family Physician 59(5):1239–45, 1999). To offer alternatives to the use of ephedrine and related drugs like amphetamines, the pharmaceutical industry has attempted with little success to develop $\beta$ receptor stimulants with more specific action limited to the promotion of lipolysis in fat cells.

Another attractive approach, to increasing rates of lipolysis has been blockade of the catecholamine $\alpha$ receptor system Lafontan, M., Berlan, M., et al., "Alpha-2-adrenoceptors in lipolysis: $\alpha 2$ antagonists and lipid mobilizing strategies", Am. J. Clinical Nutrition 55:219S-227S, 1992). This has been possible with oral use of yohimbine, another natural compound which blocks $\alpha$ receptors allowing the epinephrine and norepinephrine already present to have unopposed action at the $\beta$ receptors. While theoretically an attractive approach, and successful in promoting weight loss in dogs (Berlan, M., Galittzky, J., et al., "Anorectic effect of alpha2-antagonists in Dog: effect of acute and chronic treatment", *Pharmacology Biochemistry & Behavior* 39:313–320, 1991), the use of yohimbine has only inconsistently promoted increased weight loss in placebo controlled studies in humans (Sax, L., "Yohimbine does not affect fat distribution in men", *International Journal of Obesity* 15:561–565, 1991, and Berlin, I., Stalla-Bourdillon, A., et al., "Lack of efficacy of yohimbine in the treatment of obesity", *J. of Pharmarmocologie* (Paris) 3:343–347, 1986).

The need thus remains to develop other approaches and applications of safe natural substances to effectively promote lipolysis and facilitate weight loss.

Diindolylmethane (DIM), as well as its precursor, Indole-3-carbinol (I3C), and cogener, 2-(Indol-3-ylmethyl)-3,3'-diindolylmethane (LTR-1) are natural phytochemicals and part of the family of dietary indoles discovered in cruciferous vegetables. DIM and I3C are found in all cruciferous vegetables including broccoli, cauliflower, cabbage and Brussels sprouts (Bradfield C A and Bjeldanes L F, High performance liquid chromatographic analysis of anticarcinogenic indoles in Brassica oleracea, *J Agric. Food Chem.*, 1987, 35:46–49). DIM, together with the linear trimer, LTR-1, are formed from the precursor indole, I3C, after the enzymatic release of I3C from parent glucosinolates found in all cruciferous vegetables. Supplemental use of DIM and I3C are effective in humans in adjusting the pathways of estrogen metabolism to favor the production of 2-hydroxy estrogen metabolites (Michnovicz, J J, et al., Changes in levels of urinary estrogen metabolites after oral indole-3-carbinol treatment in humans, *J Natl Cancer Inst.*, 1997 May 21, 89(10):718–23). An increased proportion of 2-hydroxy metabolites is correlated to protection from breast cancer. This relationship has been documented in case-control studies (Ho GH, et al. Urinary 2/16 α-hydroxyestrone ratio: correlation with serum insulin-like growth factor binding protein-3 and a potential biomarker of breast cancer risk, *Ann Acad Med Singapore*, 1998, 27:294–299, and Schneider, J., et al., Abnormal oxidative metabolism of estradiol in women with breast cancer, *Proc Natl Acad Sci USA*, 1982, 79:3047-3051). The use of I3C, which converts to DIM and LTR-1 after passage through the stomach, has been the subject of a U.S. Pat. No. 5,895,787 describing the use of I3C and related dietary indoles to reduce the symptoms of fibromyalgia. Use of DIM and LTR-1 in absorption enhancing formulations for improving the balance of estrogen metabolites has been the subject of earlier investigations and provides the basis of U.S. Pat. No. 6,086,915. No prior investigations have suggested that DIM, I3C or LTR-1 might be potentially useful agents to promote lipolysis or facilitate weight loss.

3. SUMMARY OF THE INVENTION

The present invention provides methods and compositions for the promotion of weight loss and the maintenance of body weight. In particular, the present invention relates to the administration of phytochemicals, preferably I3C, DIM and/or LTR-1, for the promotion of weight loss and the maintenance of body weight by preventing weight gain. In a preferred embodiment, the dietary indole is "processed", referring to a dietary indole that has been processed according to the methods described in U.S. patent application Ser. No. 09/053,180.

Also according to the present invention, a pharmaceutical composition is provided, which comprises a phytochemical, preferably I3C, DIM and/or LTR-1, and, optionally, pharmaceutically acceptable carriers.

5. DETAILED DESCRIPTION OF THE INVENTION

The present invention is based upon the observation that phytochemicals, in particular, I3C, DIM, and LT-1, have proven to be a useful and consistent promoters of weight loss. This has facilitated weight loss and reduction in body fat in individuals who have become resistant to continuing weight loss from adherence to reduced carbohydrate diets alone. DIM, I3C, and LT-1, together with other complimentary components, like grapefruit concentrate and L-5-Hydroxy-trytophan (5HTP), have thus been found to support more active fat metabolism. Controlled trials of formulated DIM have produced evidence of more active lipolysis correlated with facilitated weight loss.

Anti-lipolytic increases in both α receptor activity and receptor number are associated with both obesity and aging (Taouis, M., Valet, P., et al., "Obesity modifies the adrenergic status of dog adipose tissue", *J. of Pharmacology and Experimental Therapeutics*, 250(3):1061-1066, 1989, and Langin, D., Portillo, M., et al., "Drop in the "atypical" β-adrenergic response and modification of the β/α2-adrenoceptor balance in fat cells from aging rabbits", *Endocrinology* 130:307–315, 1992). Thus, according to the present invention, DIM alone, DIM potentiated with grapefruit concentrate, related dietary indoles such as LTR-1 used like DIM, and DIM and LTR-1 in combination with α blocking products like yohimbe bark extract, are useful for treating obesity. This phytotherapy, when combined with a prudent carbohydrate restricted diet, defines a new nutritional system for combating adiposity. This approach is also compatible with nutritional support for the serotonin system which adds a component of appetite control. This can be achieved through additions of tryptophan, and the serotonin precursor, 5HTP, derived from *Griffonia simplicifolia* extract. 5HTP alone has been recently shown to help non-insulin dependent diabetics reduce carbohydrate intake with associated weight loss (Cangiano, C., Laviano, A., et al., "Effects of oral; 5-hydroxy-tryptophan on energy intake and macronutrient selection in non-insulin dependent diabetic patients.", *International J. of Obesity* 22:648–654, 1998).

The facilitated delivery of DIM and related indoles may be accomplished according to formulations and methods described in U.S. Pat. No. 6,086,915. The effectiveness of supplemental DIM is further supported by co-administration of DIM with grapefruit concentrate, which additionally facilitates the absorption of DIM and adds an additional fat mobilizing action.

5.1. Promotion of Weight Loss

The invention provides compositions and methods for promoting weight loss in a subject in need thereof through the administration of cruciferous phytochemicals (e.g., dietary indoles) in a pharmaceutically acceptable fashion. In a preferred embodiment, the subject is suffering from obesity. In another embodiment, the subject is overweight and has a BMI above 25 kg/m$^2$ for men and a BMI above 26 Kg/m$^2$ for women. In particular embodiments, I3C, DIM, or LTR-1, alone or in combination with each other or other compositions, are administered orally in, for example, the form of encapsulated dietary supplements.

The I3C is preferably administered at a dose of 200–500 mg per day. In alternative embodiments, I3C is administered at doses of 200–300 mg per day, 300–400 mg per day and 400–500 mg per day.

DIM is administered providing 50–500 mg per day of DIM. In preferred embodiments, the dose of DIM, I3C or LTR-1 is 50–100 mg per day, 100–200 mg per day, 200–300 mg per day, 300–400 mg per day, and 400–500 mg per day.

In a preferred embodiment, DIM is administered in an absorption enhancing formulation, as described in U.S Pat. No. 6,086,915, providing 50–600 mg per day of DIM suspended as microparticles in a starch carrier matrix. In preferred embodiments, the dose of processed DIM is 100–200 mg per day, 200–300 mg per day, 300–400 mg per day, 400–500 mg per day, and 400–600 mg per day.

The LTR-1 is preferably administered in an absorption enhancing formulation providing 50–600 mg per day of LTR-1 suspended as microparticles in a starch carrier matrix as previously described, however, the present invention contemplates the administration of any preparation of LTR-1. In a preferred embodiment, the dose of LTR-1 is 100–200 mg per day. In preferred embodiments, the dose of processed LTR-1 is 200–300 mg per day, 300–400 mg per day, 400–500 mg per day, and 400–600 mg per day.

Doses of the phytochemicals of the invention can also be calculated based upon the body weight of the subject to be treated. Doses of phytochemicals between 1 and 3 mg per kg of body weight per day are preferred. In another preferred embodiment, the phytochemicals are administered at a dose of between 1.5 and 2.5 mg per kg per day, preferably 2.0 mg per kg per day.

Alternatively, the co-administration of grapefruit, grapefruit concentrate, grapefruit juice, or grapefruit juice concentrate, or other grapefruit-derived composition and/or 5-HTP along with the indole (e.g., I3C, DIM or LTR-1) can be used to increase absorption of the phytochemicals and promote reduced carbohydrate intake for even more efficient weight loss.

In an alternative embodiment, the indole (e.g., DIM or LTR-1) is administered in the form of a liposomal sublingual spray applied directly to the oral mucosa. This liposomal suspension provides phytochemical loaded liposomes to administer the phytochemicals and create a sustained delivery system. Indole (e.g., DIM or LTR-1) containing liposomes are sequestered in the oral mucosa, allowing absorption which avoids "first pass" hepatic metabolism. The liposomal spray uses standard liposomal preparation and structural lipid ingredients. (Ranade, V. V., "Drug delivery systems. 1. Site-specific drug delivery using liposomes as carriers," *J. Clin. Pharmacol.* 29(8):685–94, 1989; Crommelin, D. J. A. and Schreir, H., "Liposomes", Colloidal Drug Delivery Systems, Kreuter, J. editor, Marcel Dekker, N.Y., 1994, p. 85).

Alternatively the indole (e.g., DIM or LTR-1) may be administered in the form of a transdermal cream applied directly to the skin. This cream utilizes various absorption enhancing emollients and consists of the indole (e.g., DIM or LTR-1) in a concentration of 1–3% by weight. It is designed as a sliming cream to encourage lipolysis and fat loss in areas of persistent adiposity such as thighs, buttocks and abdomen. (Greenway, F. L., Bray, G. A., and Heber, D., "Topical fat reduction," *Obes. Research* 3(Suppl.4):561S-568S, 1995).

In another embodiment, the method further comprises, in addition to the administration of phytochemical, limiting the subject's carbohydrate intake. In preferred embodiments, the subject's carbohydrate intake is limited to 50, 100, 150, 200, 250, 300, 350, 400, 450 and 500 mg per day.

In a preferred embodiment, the subject to be treated, even though limiting carbohydrate intake, has become resistant to losing weight through limiting of carbohydrate intake alone. In another embodiment, the subject is one who is already on a diet of limited carbohydrate intake. For such a subject, the method of the invention comprises the administration of phytochemical as described herein without additional limitation of carbohydrate intake.

The phytochemicals of the invention may be administered in any appropriate amount in any suitable galenic formulation and following any regime of administration.

The actual administered amount of phytochemical, and the amount of daily carbohydrate intake may be decided by a supervising physician and may depend on multiple factors, such as, the age, condition, file history, etc., of the patient in question.

The subject, or patient, to be treated using the methods of the invention is an animal, e.g., a mammal, and is preferably human, and can be a fetus, child, or adult. In a preferred embodiment, the subject is a dog.

5.2. Maintenance of Body Weight by Preventing Weight Gain

The invention further provides compositions and methods for maintaining body weight by preventing weight gain. In particular embodiments, one or more dietary indoles (e.g., I3C, DIM, or LTR-1), alone or in combination with each other or compositions, are administered orally in, for example, the form of encapsulated dietary supplements. For the maintenance of body weight, the phytochemicals of the invention may be administered as described in section 5.1, either at the same or lower doses. In preferred embodiments, the phytochemicals are administered at a dose of three fourths, two thirds, one half, one third and one fourth the doses described above used for weight loss. Preferred doses for maintenance of weight are 200–400 mg per day for I3C, 150–300 mg per day for processed DIM, and 150–300 mg per day for LTR-1.

In a preferred embodiment, the method of weight maintenance further comprises limiting dietary carbohydrate intake to the same or a lesser extent than used for weight loss as described above. In preferred embodiments, dietary intake is at a level 1.5 times, 2 times, 2.5 times or three times that of the amount described above used for weight loss. In another preferred embodiment, dietary carbohydrate intake is limited to the range of 150 to 400 grams of total carbohydrates per day.

The actual administered amount of phytochemical, and the amount of daily carbohydrate intake may be decided by a supervising physician and may depend on multiple factors, such as, the age, condition, file history, etc., of the patient in question.

In a particular embodiment, body weight of a subject is maintained through use of the compositions and methods of the invention after promoting weight loss in the subject. In a preferred embodiment, the weight loss to be maintained was accomplished through the methods of the invention as described in section 5.1. In another embodiment, the weight loss was accomplished through a reduction of carbohydrate intake.

The subject, or patient, to be treated using the methods of the invention is an animal, e.g., a mammal, and is preferably human, and can be a fetus, child, or adult. In a preferred embodiment, the subject is a dog.

5.3. Pharmaceutical Compositions

The pharmaceutical compositions according to the present invention preferably comprise the active constituents and one or more carriers acceptable in pharmaceutical compositions. The carrier(s) must be "acceptable" in the sense of being compatible with the other ingredients of the composition and also not deleterious to the recipient thereof.

It will be appreciated that the amounts of phytochemical required for said treatment or prevention will vary according to the route of administration, the amount subject is overweight, the degree of obesity to be treated, the condition, age, file history of the subject, and the galenic formulation of the pharmaceutical composition, etc.

Preferably, the phytochemical used in the invention has been processed to enhance bioavailability, as is described in U.S. Pat. No. 6,086,915. So processed DIM or LTR-1 is referred to as "processed DIM" and "processed LTR-1", respectively. However, any suitable preparation of phytochemical can be used in the methods and compositions of the invention.

The following is a list of ingredients useful for formulating processed DIM or LTR-1:

1. About 10 to about 40 percent by weight of LTR-1 or DIM.
2. About 10 to about 40 percent by weight of the following, alone or in combination: vitamin E succinate polyethylene glycol 1000; vitamin E succinate Polyethylene glycols with polyethylene glycol (with a molecular weight range of 400–2000); other polyethylene glycol esters such as those formed by fatty acids such as oleic acid or stearic acid; polyvinylpyrrolidones; polyvinylpolypyrrolidones; Poloxamer 188, Tweens; or Spans.
3. About 5 to about 20 percent by weight of the following, alone or in combination: phosphatidyl choline (derived from soy lecithin and supplied as Phospholipon SOG from Rhone Poulenc Rorer); dioleoyl phosphatidylcholine; phoshatidylglycerol; dioleoylphosphatidylglycerol; dimyristoylphosphatidylcholine; dipalmitoylphosphatidylcholine; phosphatidylethalolamines; phosphatidylserines; or sphingomyelins; or other sources of phospholipids as those from purified Milk Fat Globule Membrane; glycerolesters; poly glycerol esters; or ethoxylated castor oil.
4. About 15 to about 30 percent by weight of the following, alone or in combination: hexanol; ethanol; butanol; heptanol; 2-methyl-1-pentanol; various ketone solvents that would be acceptable in foods such as methyl ethyl ketone, acetone and others; propylene glycol; and certain ester solvents such as ethyl acetate.
5. About 20 to about 40 percent by weight of the following, alone or in combination: modified starch such as Capsul™ Starch from National Starch, Inc.; methylcellulose; hydroxypropyl methylcellulose; hydroxyethylcellulose; hydroxypropylethylcellulose; pectin; gum arabic; gelatin; or other polymeric matrix-forming preparation known to those skilled in the art, soluble in water and, suitable for spray drying.
6. About 0.5 to about 35 percent by weight of the following, alone or in combination: aerosil 200; or any other flow enhancing excipient from silica, or related salt, known to those skilled in the art.

The following is a detailed method of formulating processed DIM:

1. 6.75 kg of TPGS is heated just beyond its melting point with constant stirring in a heated vessel ("First vessel").
2. 9.38 kg of hexanol and 9.83 kg of jet milled DIM is added to the first vessel and the mixture stirred to a uniform suspension at 70° C. 1.4 kg of phosphatidyl choline is then added.
3. In a second larger vessel, 185 L of water and 10.7 kg of starch are thoroughly mixed with a Cowles blade. This mixture is neutralized to pH 7 with a small amount of sodium carbonate and then heated to 75° C. and stirred for 1 hour.
4. The contents of the first vessel is added to the starch mixture in the second larger vessel and thoroughly mixed with a homogenizing rotor/stator type mixer at moderate speed for 15 minutes.
5. The mixture from step 4 is spray dried with a small amount (approximately 0.5%) of hydrophilic silica to provide a free flowing powder of finely dispersed microparticles containing the co-precipitated TPGS, phosphatidyl choline and DIM in an amorphous, non-crystalline structure.
6. The flowable powder product is collected and stored in evacuated foil sacks, after de-aerating and flushing with nitrogen.
7. Analysis of presence of unchanged dietary ingredient, reveals about 30 to about 33 percent by weight of DIM.

The procedure of making processed DIM may be summarized as follows:

(a) heating one or more solubilizing emulsifiers selected from the group consisting of vitamin E succinate polyethylene glycol 1000, polyvinylpyrrolidone, polyoxyethylene stearate, sodium cholate, deoxycholate and taurocholate;

(b) adding to the product of step (a) a solvent and a surfactant phospholipid selected from the group consisting of phosphatidyl choline, dioleoyl phosphatidyl choline, phosphatidylglycerol, dioleoylphosphatidylglycerol, dimyristoylphosphatidylcholine, dipalitoylphosphatidylcholine, phosphatidylethanolamine, phosphatidylserine and sphingomyelin to produce a solution;

(c) dissolving in the solution of step (b) LTR-1 and/or DIM;

(d) adding to the solution of step (c) a solution containing an encapsulator;

(e) mixing the solution produced in step (d) to produce a microdispersion with a particle size of 5 microns or less; and (f) spray drying the resulting mixture to leave a solid hydrophobic phytochemical composition.

In general, a suitable (therapeutically effective) amount of I3C is 300–500 mg per day. DIM is preferably administered in an absorption enhancing formulation, as described in U.S. Pat. No. 6,086,915, at 100–200 mg per day suspended as microparticles in a starch carrier matrix. The LTR-1 is preferably administered in an absorption enhancing formulation at 100–200 mg per day suspended as microparticles in a starch carrier matrix. The actually administered amounts of phytochemical may be decided by a supervising physician. The phytochemicals of the invention may be administered alone or in combination with one another, and/or with other compositions. The combinations of one or more phytochemicals and other compositions can be in the same composition for administering in combination concurrently, or in different compositions for administering concurrently but separately, or sequentially.

Therapeutic formulations include those suitable for parenteral (including intramuscular and intravenous), oral, rectal or intradermal administration, although oral administration is the preferred route. Thus, the pharmaceutical composition may be formulated as tablets, pills, syrups, capsules, suppositories, formulations for transdermal application, liposomal sprays, powders, especially lyophilized powders for reconstitution with a carrier for intravenous administration, etc.

The term "carrier" refers to a diluent, adjuvant, excipient, or vehicle with which the therapeutic is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; a glidant, such as colloidal silicon dioxide; a sweetening agent, such as sucrose or saccharin; and/or a flavoring agent, such as peppermint, methyl salicylate, or orange flavoring.

Therapeutic formulations suitable for oral administration, e.g., tablets and pills, may be obtained by compression or molding, optionally with one or more accessory ingredients. Compressed tablets may be prepared by mixing phytochemicals, and compressing this mixture in a suitable apparatus into tablets having a suitable size. Prior to the mixing, the phytochemical may be mixed with a binder, a lubricant, an inert diluent and/or a disintegrating agent.

In a preferred embodiment, phytochemical is mixed with a binder, such as microcrystalline cellulose, and a surfactant, such as sodium lauryl sulphate until a homogeneous mixture is obtained. Subsequently, another binder, such as polyvidone, is transferred to the mixture under stirring. This mixture is passed through granulating sieves and dried by desiccation before compression into tablets in a standard compressing apparatus.

A tablet may be coated or uncoated. An uncoated tablet may be scored. A coated tablet may be coated with sugar, shellac, film or other enteric coating agents.

Therapeutic formulations suitable for parenteral administration include sterile solutions or suspensions of the active constituents. An aqueous or oily carrier may be used. Such carriers can be sterile liquids, such as water and oils, including those of petroleum, animal, vegetable or synthetic origin, such as peanut oil, soybean oil, mineral oil, sesame oil and the like. Formulations for parenteral administration also include a lyophilized powder comprising phytochemical that is to be reconstituted by dissolving or suspending in a pharmaceutically acceptable carrier that dissolves or disperses said phytochemical.

When the pharmaceutical composition is a capsule, it may contain a liquid carrier, such as a fatty oil, e.g., cacao butter.

Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. These compositions can take the form of solutions, suspensions, emulsion, tablets, pills, capsules, powders, sustained-release formulations and the like. The composition can be formulated as a suppository, with traditional binders and carriers such as triglycerides.

In yet another embodiment, the therapeutic compound can be delivered in a controlled release system. In one embodiment, a pump may be used (see Langer, supra; Sefton, *CRC Crit. Ref. Biomed. Eng.* 14:201 (1987); Buchwald et al., *Surgery* 88:507 (1980); Saudek et al., *N. Engl. J. Med.* 10 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)).

Other controlled release systems are discussed in the review by Langer (Science 249:1527–1533 (1990)).

In one embodiment of the pharmaceutical composition according to the invention, two or more active constituents are comprised as separate entities. The two entities may be administered simultaneously or sequentially.

The invention also provides a pack or kit comprising one or more containers filled with one or more of the ingredients of the pharmaceutical compositions of the invention. Optionally associated with such container(s) can be a notice in the form prescribed by a governmental agency regulating the manufacture, use or sale of the pharmaceutical composition, or biological products, which notice reflects approval by the agency of manufacture, use or sale for human administration.

The invention is further explained by the following illustrative examples.

6. Example: Manufacture of Processed DIM or LTR-1 for Enhanced Oral Bioavailability Preparation of processed DIM and LTR-1 was accomplished according to the steps outlined in U.S. patent application Ser. No. 09/053,180. Briefly, this included mixture of about 10–40% by final weight of either DIM or LTR-1 with about 10–40% by final weight of vitamin E polyethylene glycol 1000 succinate(Vitamin-E-TPGS, Eastman Chemical), 2–20% by final weight, phosphatidyl choline (Phospholipon 50G, Rhone Poulenc) and 15–30% by final weight hexanol. This mixture was made homogeneous by mixing. The homogeneous mixture of indoles and other oil soluble substituents listed above was added to a solution of modified starch in water (Capsul Starch from National Starch, Inc.). The starch component forms form from 30–70% of the final dry weight of the product. The well dispersed final combined mixture was then subjected to spray drying. The resultant product was a fine powder containing either DIM or LTR-1 contained within the starch particles.

7. Example: Manufacture of I3C Capsules Using Pure I3C

Pure Indole-3-carbinol (I3C) was obtained from standard suppliers (Sabinsa, Inc or Designed Nutritional Products, Inc.). Capsules containing 300–500 mg were manufactured by placing that amount of I3C into opaque gelatin capsules.

Capsules containing 150–300 mg of processed DIM, as produced according to the steps described in example 1., were made by mixing the processed DIM with microcrystaline cellulose and placing the mixed powder into opaque gelatin capsules.

Similarly, capsules containing 150–300 mg of processed LTR-1, as produced according to the steps described in example 1., were made by mixing the processed LTR-1 with microcrystaline cellulose and placing the mixed powder into opaque gelatin capsules.

8. Example: Manufacture of DIM or LTR-1 in a Cream for Transdermal Delivery

For the aqueous phase of the emulsion, a mixture of 70 grams of propylene glycol and 633 grams of water is heated to 95° C. The oil phase of the emulsion is prepared by heating a mixture of the following to 105° C: 30 grams cetostearyl alcohol (Alfol 16/18, Vista ), 30 grams hydrogenated soy monoglyceride (Myverol 18–06, Quest), 30 g of a mixture of polyoxyethylene stearic acid ester and mono- and di-glycerides of fatty acids (Arlacel 165, ICI), 10 grams polyethylene (Epolene N-34, Eastman), and 50 g. of squalene. The active ingredient phase is prepared separately also by gently heating to about 63° C. a mixture of the following to uniformity: 30 g d-α-tocopherol polyethylene glycol 1000 succinate (Vitamin E TPGS, Eastman), 50 g isopropyl myristate, and 15 g of DIM or 15 g of LTR-1. The above oil phase is added to the aqueous phase using a rotor/stator type homogenizer at moderate speed. The mixture is cooled to 75° C. and 50 grams of lemon oil is added with low speed mixing followed by addition of the active ingredient phase. Lastly, 2 g of a 3:1 mixture of methyl paraben to propyl paraben is added to the emulsion. This mixture is transferred to the reservoir of a high pressure homogenizer such as the Microfluidics ‰ Model 110Y. The emulsion is passed through the homogenizer approximately five times at 15,000 psi operating pressure that is sufficient to form a cream of the desired consistency which will not separate on standing.

9. Example: Manufacture of DIM or LTR-1 in a Liposomal Spray for Sublingual and Oral Mucosal Delivery A standard liposomal preparation technique was used to prepare a liposomal suspension of DIM and separately, a liposomal preparation of LTR-1. Briefly, propylene glycol (7.0 gms) was heated to 92° C. on a water bath, 8 grams of partially hydrogenated pure egg yolk lecithin, and 320 mg of stearylamine were added and dissolved to give a clear liquid. To this liquid was added 500 mg of jet milled DIM. This translucent solution was added to 200 ml of a 1% aqueous solution of dextran T 40 pre-warmed to 55° C. and the mixture was stirred in a propeller mixer at 50° C. for 3 minutes after which it was cooled to room temperature. This procedure yielded an off-white, dextran T 40/liposome suspension, thus encapsulating the DIM.

Equivalent steps were undertaken to prepare a lipsomal suspension encapsulating LTR-1.

10. Example: Manufacture of a Food Bar Containing Grapefruit Concentrate, Processed DIM or LTR-1, and the Serotonin Precursors, Tryptophan and 5-Hydroxy-Trytophan (5HTP)

Food bars were manufactured by using a standard food processor to which was added the following ingredients: organic grapefruit rind (100 gms), organic spirulina powder (50 grams), dried *Griffonia simplicifolia* extract (1 gm). 3 grams of processed DIM containing 1 gm of microencapsulated DIM by weight was then added to the mixture and homogeneously mixed. After mixing, whey protein powder, calcium caseinate, maltodextrin, grapefruit oil, brown sugar, and natural flavoring were added with further mixing to provide bulk and consistency for formation into food bars. The final mixture was extruded to form 10 food bars each containing 100 mg of DIM.

Equivalent steps were undertaken to produce food bars containing LTR-1. Processed LTR-1 was substituted for processed DIM, producing 10 food bars each containing 100 mg of LTR-1.

11. Example: Weight Loss with DIM

S. G. is 50 years old and weighed 213 pounds at the time of her referral. She has been post menopausal for 2 years and takes premarin 0.625 mg/day. A carbohydrate restricted diet program including a daily exercise component was initiated. Using urine dip-sticks for determination of ketonuria, the daily carbohydrate intake which allowed minimal ketosis was determined to be 20 grams. The presence of ketones in urine is an accepted measure of active metabolism of stored fat or "lipolysis". Glycerol released from fat cells along with stored fatty acids during lipolysis is directly converted into ketones which appear in the urine. (Williamson, D. H., Postgraduate Medical Journal, June Suppl., pages 371–375, 1971; Nosadini R, Avogaro A, et al, Diabetes Metab Rev 1989 May; 5(3):299–319). Supplementation with bioavailable DIM was introduced at 300 mg/day and subsequently increased to 450 mg/day.

After the introduction of DIM, carbohydrate consumption was able to be increased to 50 gms/day and still be associated with ketosis. Without instituting caloric restriction in addition to the elimination of carbohydrates, the patient proceeded to lose 10% of her body weight over a period of 6 weeks. Following this weight loss of 21 pounds, she reduced her supplemental use of DIM to 300 mg/day and liberalized her carbohydrate intake to 150 grams per day. This allowed for a significant increase in high fiber vegetables. A continued, though more gradual, weight loss has been noted during her maintenance regimen.

| | Ketosis (Urine Dipstick Reading) | | |
|---|---|---|---|
| Subject | Carbohydrate Intake (gm/day) | Diet Alone | Diet plus processed DIM |
| S.G. | 20 | + | ++ |
| | 50 | − | + |

12. Example: Processed DIM used on Combination with Grapefruit Concentrare by Overweight Men Subjects RB and PS are middle aged men troubled by persistent overweight. Each had adhered to a low carbohydrate diet and achieved and initial weight loss of approximately 10 pounds. This was followed by resistance to further weight loss despite adherence to the diet and regular, moderate aerobic exercise.

Addition of processed DIM capsules resulted in a resumption of weight loss in both cases. Monitoring lipolysis as reflected in urine dipsticks for ketones demonstrated increased ketosis at a given carbohydrate intake and persisting ketosis at increased carbohydrate intake for both subjects. These results are summarized in the following charts.

Subsequent to these observations addition of grapefruit concentrate in the form of reconstituted grapefruit juice (Minute Maid) was added to the subjects weight loss dietary regimen. In each case, the addition of one eight ounce glass of grapefruit juice twice daily together with two capsules of processed DIM (300 mg of total supplement weight) resulted in further weight loss and a further increase in the degree of ketosis documented on urine dipstick testing. These results are summarized in the following chart.

| | | Level of Ketosis (Urine Dipstick Reading) | | |
|---|---|---|---|---|
| Subject | Carbohydrate Intake (gms/day) | Diet Alone | Diet and DIM | Diet, GFJ, and DIM |
| P.S. | 50 | + | ++ | |
| | 100 | 0 | + | ++ |
| R.B. | 20 | + | ++ | |
| | 40 | 0 | + | ++ |

After cessation of the weight loss program, dietary carbohydrate intake was increased to typical amounts and processed DIM was continued at one half the dose used during the weight loss program. The increased carbohydrate intake corresponded to 40–50% of total daily calories from carbohydrate sources. This use of processed DIM resulted in maintenance of a stable weight at the level achieved following the weight loss program.

13. Example: Weight Loss Study Demonstrating Statistically Significant Association Between DIM Effect of Ketosis and Weight Loss Acheived by Volunteer Subjects A 6-week study was conducted by 18 moderately overweight individuals who consumed 150–600 mg of a processed DIM supplement containing 30% DIM by weight. Processed DIM was prepared as described in U.S. patent application Ser. No. 09/053,180, and as briefly described in section 6. Subjects were on a monitored, carbohydrate restricted diet. Each subject documented all carbohydrates consumed and the presence and level of ketosis based on daily urine dipstick testing for ketones. (Keto-Diastix, Bayer Corp.)

In this study individuals on a carbohydrate restricted diet first determined their Critical Carbohydrate Level (CCL). This was established by first demonstrating ketosis with at least a small reading on urine dipsticks following at least 3 days of documented carbohydrate intake and daily urine testing. (Readings include: Negative; Trace; Small; Moderate; Large; Largest) Following this, carbohydrate intake was increased by 10–15 grams per day until a negative urine test was obtained. This defined an individuals CCL with a subject-specific carbohydrate intake just sufficient to eliminate ketosis and lipolysis. This process was repeated over a period of days to confirm the accuracy of an individual's CCL in grams of carbohydrate ingested per day.

Following the determination of an individuals CCL, processed DIM was started at 2 caps (300mg) per day for one week and carbohydrate intake was held constant at close to the CCL level for each individual. After one week on processed DIM, every individual showed positive urine strips indicative of active lipolysis and daily carbohydrate intake was increased by 10–15 grams per day. This was continued until a negative urine test was again demonstrated and confirmed at the higher carbohydrate level. This determined each subject's CCL on processed DIM. The CCL on processed DIM was determined again after increasing the processed DIM dose to 3 caps and then to 4 caps in a few of the subjects. Body weights were followed by weekly weighing using a qualified office scale.

Figure 1:
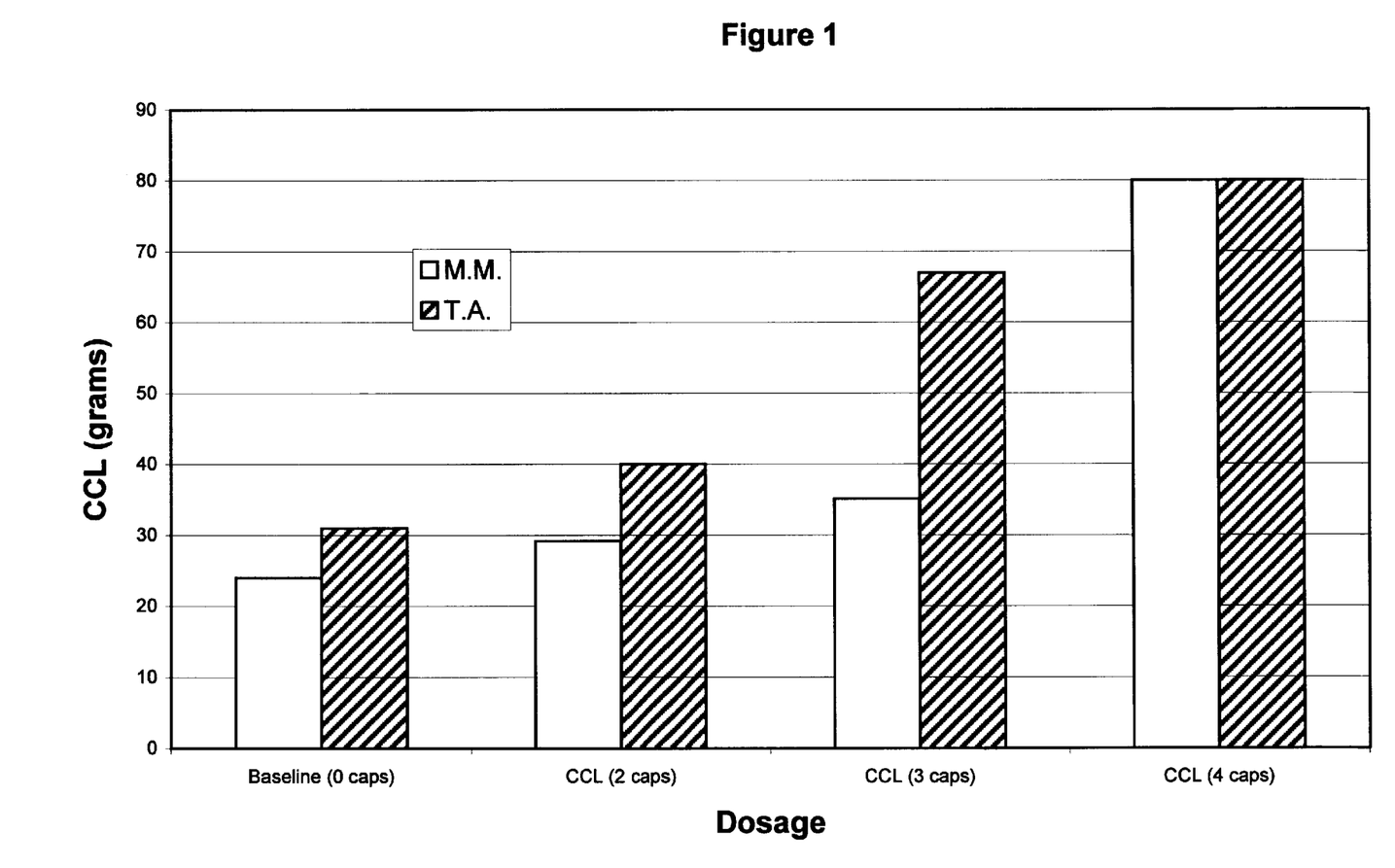
FIG. 1 depicts the dose response from processed DIM presented as the increasing level of carbohydrate intake ("Critical Carbohydrate Level [CCL]") associated with persisting ketosis.
Figure 2:
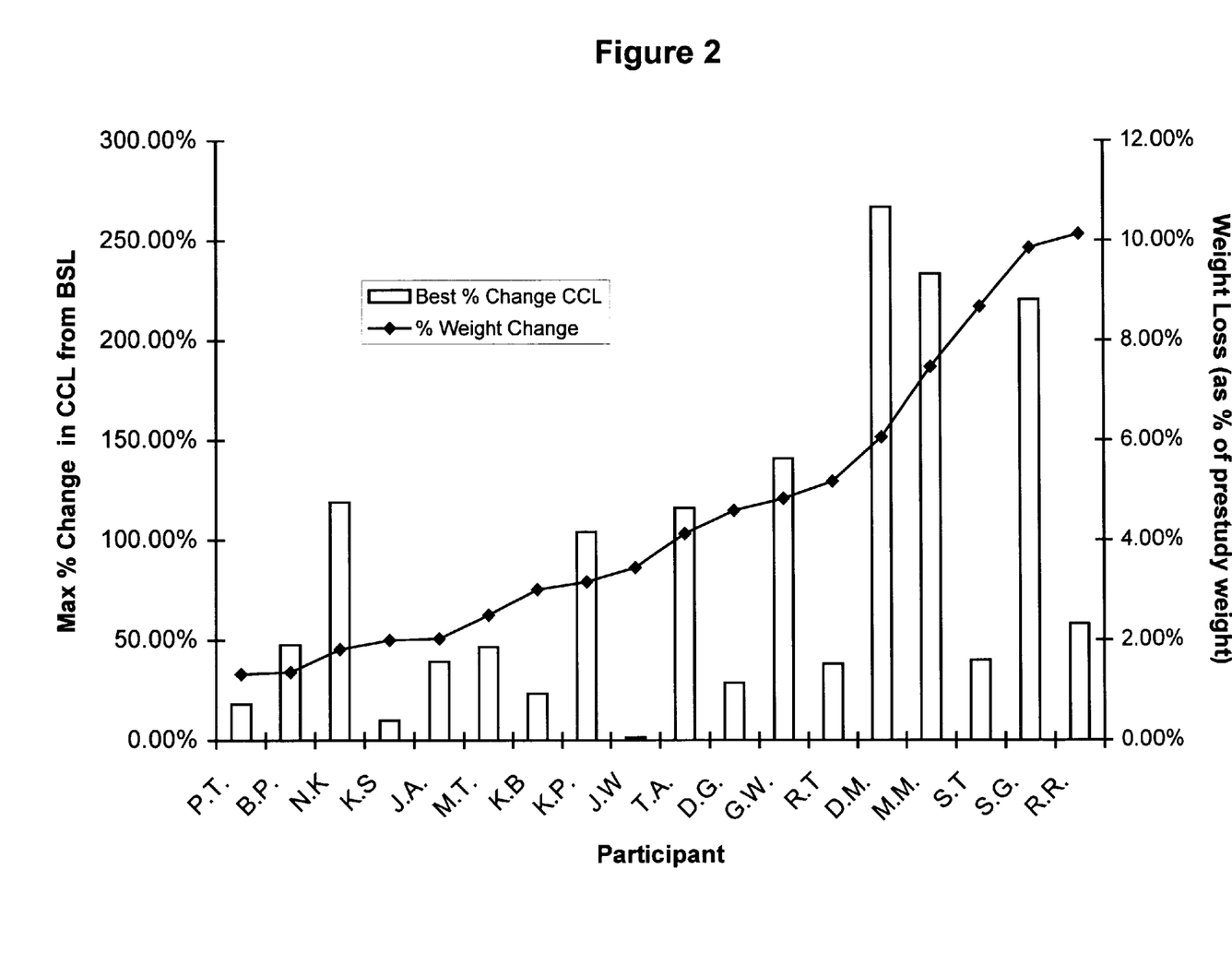
FIG. 2 depicts the effect of processed DIM showing the increase in carbohydrate intake (Max % Change in CCL ["Critical Carbohydrate Level"] from BSL [Baseline]) and the weight loss acheived (Weight Loss as % of pre-study weight) for each subject.
Figure 3:
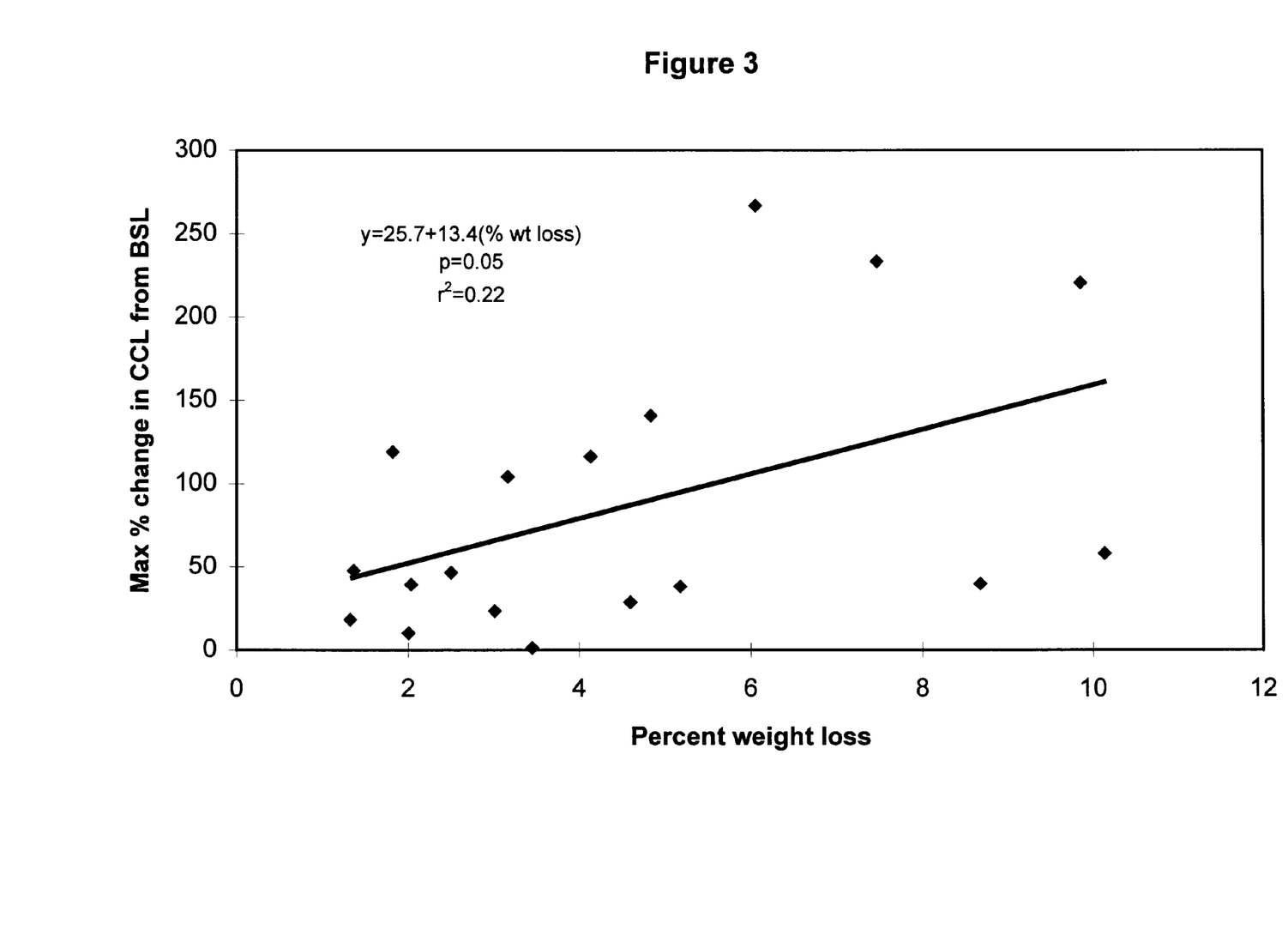
FIG. 3 depicts the statistically significant correlation of weight loss achieved (Percent Weight Loss) and the effect of processed DIM as measured by the increase in carbohydrate intake still associated with ketosis (Max % Change in CCL ["Critical Carbohydrate Level"] from BSL [Baseline])
Figure 4:
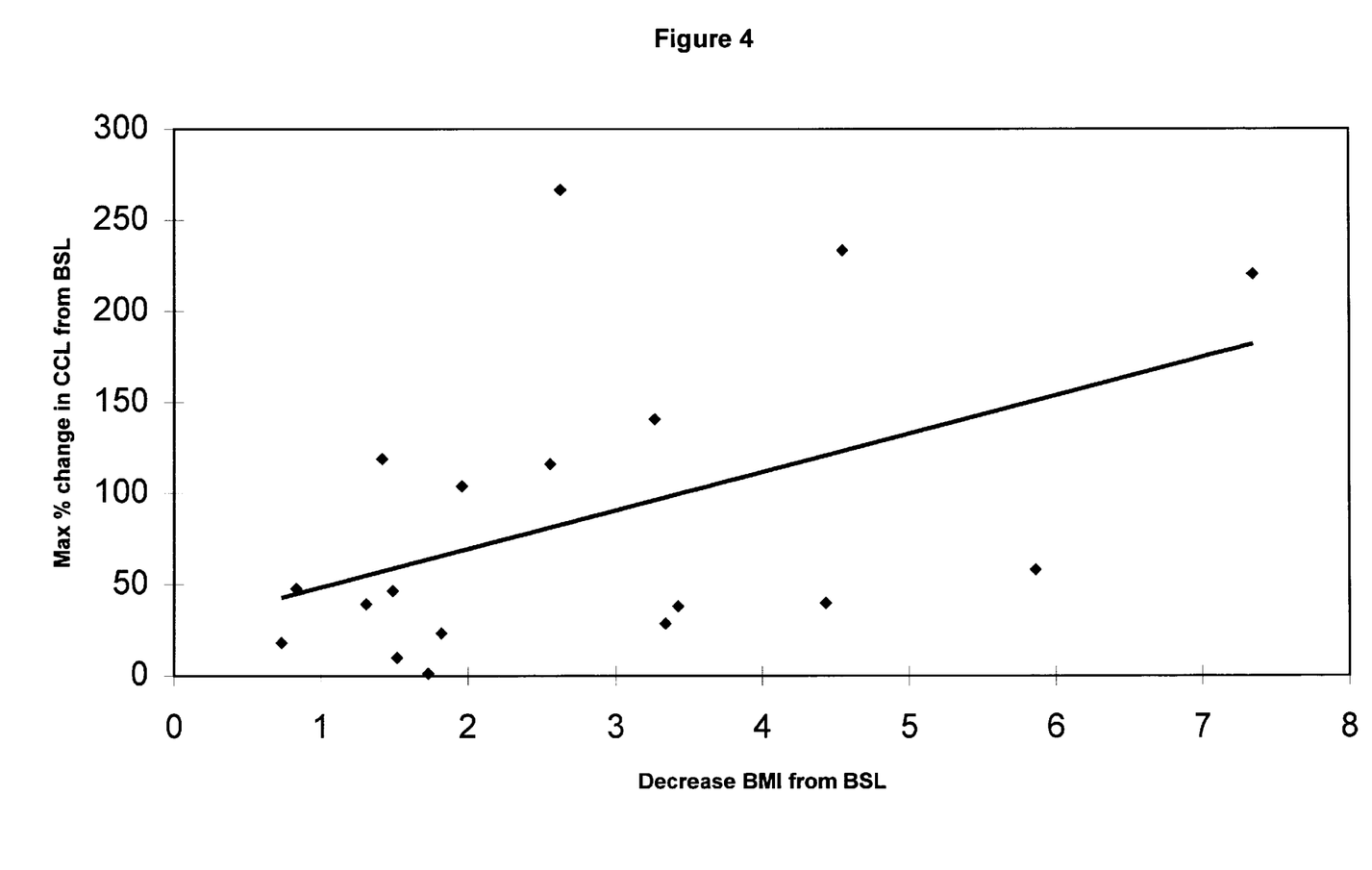
FIG. 4 depicts the statistically significant correlation of decrease in Body Mass Index (BMI) and the effect of processed DIM as measured by the increase in carbohydrate intake still associated with ketosis (Max % Change in CCL ["Critical Carbohydrate Level"] from BSL [Baseline]). This demonstrates that the Processed DIM effect is independent of height.

The documented increase in CCL for each subject was standardized as the Maximum % Change in CCL from Baseline by computing the percent increase in CCL while taking processed DIM over the baseline value. Data from two individuals is resented in FIG. 1. This figure demonstrates that increased doses of processed DIM allow for progressively greater levels of carbohydrate intake to be associated with ketosis. The data from all subjects is presented in FIG. 2, showing both the maximal percentage increase in CCL for each subject and associated weight loss for each subject during the 6 weeks of the study. When results for all subjects were analyzed, the correlation of percent increase in CCL and percent change in body weight was significant at $p=0.05$, confirming the contribution of processed DIM to enhanced lipolysis and weight loss. This is shown in FIG. 3. This correlation of the effect from processed DIM (% Change in CCL) to weight loss as reflected in the observed decrease in Body Mass Index (The decrease in BMI from baseline [BSL]) remained significant as shown in FIG. 4. FIG. 4 demonstrates that the processed DIM effect in promoting weight loss was independent of each subject's height.

The dose of processed DIM used in the study ranged from about 3–4 mg/kg/day at 2 caps to 4.5–6.4 mg/kg at 3 caps. Since processed DIM is 30% DIM by weight, this dosage range employed extended from about 1 to 2.1 mg/kg/day of DIM.

In summary, these results demonstrate both a dose related and statistically significant action of processed DIM in promoting weight loss. Further, these results document an effect of processed DIM which promotes weight loss at progressively increased carbohydrate intakes and which is associated with active lipolysis.

What is claimed is:

1. A method of promoting weight loss in a subject in need thereof comprising administering to the subject an amount of a dietary indole effective to promote weight loss.

2. The method according to claim 1 wherein the dietary indole is selected from the group consisting of I3C, DIM and LTR-1.

3. The method of claim 2 wherein the dietary indole is DIM.

4. The method of claim 3, wherein the DIM is suspended as microparticles in a starch carrier matrix.

5. The method of claim 1, further comprising limiting the carbohydrate intake of the subject to an amount effective to promote weight loss.

6. The method of claim 1, further comprising limiting the carbohydrate intake of the subject to less than 500 grams per day.

7. A pharmaceutical composition comprising an amount of a dietary indole effective to promote weight loss.

8. The composition of claim 7 wherein the dietary indole is selected from the group consisting of I3C, DIM and LTR-1.

9. The composition of claim 8 wherein the dietary indole is DIM.

10. The composition of claim 9, wherein the DIM is suspended as microparticles in a starch carrier matrix.

11. The composition of claim 7, wherein the composition is formulated for oral administration.

12. The composition of claim 7, wherein the dietary supplement composition is formulated as a pill.

13. The composition of claim 7, wherein the dietary supplement composition is formulated as a tablet.

14. The composition of claim 7, wherein the dietary supplement composition is formulated as a capsule.

15. The composition of claim 7, wherein the dietary supplement composition is formulated as a cream.

16. The composition of claim 7, wherein the dietary supplement composition is formulated as a liposomal spray.

17. A method of treating weight gain in a subject in need thereof comprising administering to the subject an amount of a dietary indole effective to treat weight gain.

18. The method according to claim 17 wherein the dietary indole is selected from the group consisting of I3C, DIM and LTR-1.

19. The method of claim 18 wherein the dietary indole is DIM.

20. The method of claim 19, wherein the DIM is suspended as microparticles in a starch carrier matrix.

21. The method of claim 17, further comprising limiting the carbohydrate intake of the subject to an amount effective to treat weight gain.

22. The method of claims 21, further comprising limiting the carbohydrate intake of the subject to less than 500 grams per day.

23. A pharmaceutical composition comprising an amount of a dietary indole effective to treat weight gain.

24. The composition of claim 23 wherein the dietary indole is selected from the group consisting of I3C, DIM and LTR-1.

25. The composition of claim 24 wherein the dietary indole is DIM.

26. The composition of claim 25, wherein the DIM is suspended as microparticles in a starch carrier matrix.

27. The composition of claim 23, wherein the composition is formulated for oral administration.

28. The composition of claim 23, wherein the dietary supplement composition is formulated as a pill.

29. The composition of claim 23, wherein the dietary supplement composition is formulated as a tablet.

30. The composition of claim 23, wherein the dietary supplement composition is formulated as a capsule.

31. The composition according to claim 23, wherein the dietary supplement composition is formulated as a cream.

32. The composition according to claim 23, wherein the dietary supplement composition is formulated as a liposomal spray.

33. The method of claims 1 or 17, further comprising administering grapefruit, grapefruit concentrate, grapefruit juice, or grapefruit juice concentrate.

34. The composition of claims 7 or 23, further comprising grapefruit, grapefruit concentrate, grapefruit juice, or grapefruit juice concentrate.

* * * * *